United States Patent [19]

Miura et al.

[11] Patent Number: 4,851,590

[45] Date of Patent: Jul. 25, 1989

[54] METHOD OF PURIFYING 2,4-XYLENOL

[75] Inventors: Tohru Miura; Katsuju Watanabe; Hitoshi Nakayama; Masayuki Furuya; Teruyuki Nagata, all of Fukuoka, Japan

[73] Assignee: Mitsui Toatsu Chemicals, Inc., Tokyo, Japan

[21] Appl. No.: 199,750

[22] Filed: May 27, 1988

[30] Foreign Application Priority Data

May 29, 1987 [JP] Japan .................................. 62-131694
May 12, 1988 [JP] Japan .................................. 63-115119

[51] Int. Cl.$^4$ ....................... C07C 37/70; C07C 37/68
[52] U.S. Cl. ..................................... 568/750; 568/753
[58] Field of Search ............................... 568/750, 753

[56] References Cited

U.S. PATENT DOCUMENTS 2,917,487 12/1959 Jones et al. .......................... 568/750
4,236,030 11/1980 Selwitz et al. ....................... 568/750
4,247,719 1/1981 Buck et al. .......................... 568/750
4,249,026 2/1981 Dodd .................................. 568/750

Primary Examiner—Werren B. Lone
Attorney, Agent, or Firm—Millen, White & Zelano

[57] ABSTRACT 2,4-Xylenol can be obtained in high yield and high purity from a crude 2,4-xylenol isomer mixture containing 2,5-xylenol by selectively reacting the 2,5-xylenol with an aldehyde in the presence of an aromatic sulfonic acid, thereby converting the 2,5-xylenol into a xylenol-aldehyde condensate and, subsequently, separating the 2,4-xylenol, e.g., by distillation.

19 Claims, No Drawings

METHOD OF PURIFYING 2,4-XYLENOL

BACKGROUND OF THE INVENTION

1. Field of the Invention

The present invention relates to a method for purifying a crude 2,4-xylenol mixture containing 2,5xylenol, more specifically, to a method for producing 2,4-xylenol of high purity from crude 2,4-xylenol containing 2,5-xylenol.

2,4-Xylenol is useful as the starting material for synthetic resins, adhesives, insecticides, antioxidants, herbicides, dyes, etc. and has been produced and used in great amounts. Depending on the specific end use, products of high purity are required.

2. Description of the Prior Art

Xylenol includes six isomers, that is, 2,3-xylenol, 2,4-xylenol, 2,5-xylenol, 2,6-xylenol, 3,4-xylenol and 3,5-xylenol. Since the boiling points of these isomers are close to each other, it is extremely difficult to efficiently separate the respective isomers from a mixture thereof by distillation. Particularly, since the boiling points of 2,4-xylenol and 2,5-xylenol are substantially identical, they cannot be separated by mere rectification. Consequently, a 2,4-xylenol with a purity of about 90–95% at the highest is the purest commercially available at present.

Various methods of separating 2,4-xylenol and 2,5-xylenol have been proposed. For instance, one separating and purifying method utilizes the fact that 2,4-xylenol forms a molecular compound with methyl quinoline, aniline, toluidine, etc. (for example, see U.S. Pat. No. 2,526,807); another involves alkylation into a tert-butylated product by reaction with isobutylene, separating the tert-butylated product by fractional distillation and then carrying out dealkylation in the presence of an acid (for example, see British Patent No. 582,057); another separating method involves sulfonation and, successively, carrying out partial hydrolysis with super heated steam (for example, see U.S. Pat. No. 2,327,312); and another method uses an adsorbent, such as a molecular sieve, calcium oxide or zeolite.

Another method involves reacting a mixture of xylenol isomers with formaldehyde in the presence of a strong acid, such as hydrochloric acid, or a strong base such as sodium hydroxide and then separating only the 2,5-xylenol in the form of a xylenol-formalin resin (for example, see U.S. Pat. No. 2,917,487).

U.S. Pat. No. 2,917,487 discloses conducted the condensation reaction at temperatures of 50°–100° C. using hydrochloric acid as a catalyst in an amount of 2–8% by weight to obtain purified 2,4-xylenol with a purity of 95.1% at the highest and a purity-converted yield of 67.3%. Such purity and yield are not fully satisfactory, particularly because, depending on contemplated use of 2,4-xylenol, purification products of a purity higher than 95% and, desirably, from 98 to 99% may at times be needed. 2,4-Xylenol of such a high purity cannot be obtained by the method of the above-cited U.S. patent without reducing the yield of 2,4-xylenol to an unacceptably low level. In addition, according to this method, after selectively condensing only the 2,5-xylenol with formalin in the presence of the acid catalyst, the reaction mass is distilled under heating to separate the 2,4-xylenol and the acid used for the condensation reaction is removed by water washing. However, the removal of hydrochloric acid with water washing causes a wastewater treatment problem at an industrial level. This problem can be overcome by removing the hydrochloric acid through neutralization by adding an alkali such as sodium hydroxide to the reaction mass after the condensation reaction. However, in this case, since the reaction mass containing the alkali metal is heated, care must be taken in view of the handling safety. Further, the loss in 2,4-xylenol is not negligible.

For the foregoing reasons, it is presently very difficult to obtain 2,4-xylenol with high purity in industrial amounts.

SUMMARY OF THE INVENTION

An object of the present invention is to provide an industrial method for the purification of 2,4-xylenol by separating 2,5-xylenol from a crude 2,4-xylenol mixture which contains 2,5-xylenol.

A second object of the present invention is to provide an improved purification method of obtaining 2,4-xylenol with higher purity from such a mixture without reducing the yield thereof.

Upon further study of the specification and appended claims, further objects and advantages of this invention will become apparent to those skilled in the art.

The foregoing objects can be attained by reacting a crude 2,4-xylenol mixture containing 2,5-xylenol with an aldehyde in the presence of an aromatic sulfonic acid and separating the 2,5-xylenol from the 2,4-xylenol in the form of a xylenol-aldehyde condensate.

DETAILED DESCRIPTION OF THE INVENTION

The present inventors have extensively studied the purification of 2,4-xylenol by removing 2,5-xylenol contained in a crude 2,4-xylenol isomer mixture and have found that when the crude mixture is reacted with an aldehyde in the presence of an aromatic sulfonic acid as an acid catalyst, 2,5-xylenol can preferentially be reacted with the aldehyde at a relatively low temperature.

In the method of the present invention, the aldehyde added to the reaction system selectively reacts with the 2,5-xylenol in the crude 2,4-xylenol mixture and scarcely any is consumed by reaction with the 2,4-xylenol. Accordingly, 2,4-xylenol with purity higher than 95% can be obtained without separation loss of the 2,4-xylenol.

Furthermore, if water is present in the reaction system, 2,4-xylenol can be obtained with a higher purity and higher yield. More specifically, 2,4-xylenol can be obtained in higher purity and in higher yield if the reaction with the aldehyde is conducted in the presence of water, preferably in an amount not exceeding the saturation solubility based on the entire amount of xylenol to be processed in the reaction system together with the aromatic sulfonic acid. Also, the reaction with the aldehyde can be conducted in a wide range of temperatures by properly selecting the amount of water added. The present invention is based on these findings.

In carrying out the method according to the present invention, only the 2,5-xylenol is reacted selectively with an aldehyde in the presence of an aromatic sulfonic acid catalyst. The acid catalyst remaining in the reaction mass is then removed by any conventional method, e.g., washing or neutralization. Thereafter, the 2,4-xylenol is separated from the reaction mass, e.g., by fractional distillation to recover 2,4-xylenol as the distillate and separating the thus-produced 2,5-xylenol-aldehyde condensates as the still residue. In this way, 2,4-xylenol of high purity can be obtained with high yield.

In the method according to the present invention, although there is no particular restriction on the composition of the starting crude 2,4-xylenol isomer mixture, the method of the present invention is particularly effective for the purification of 2,4-xylenol of from 80–95% purity, e.g., 90–95%, to 95% or higher purity, e.g., 96–99.9%. In many cases, crude xylenols containing 80–95% of 2,4-xylenol are used as the starting material.

Because 2,5-xylenol is usually the predominant contaminant in crude 2,4-xylenol, the present invention is directed primarily to its removal. Thus, a preferred starting crude 2,4-xylenol consists essentially (98% or more) of 2,4-xylenol (80–95%) and the remainder 2,5-xylenol, except for minor amounts, e.g., up to about 1–2% by weight of other impurities. However, other xylenol isomers, such as 2,3-xylenol, can also be separated through the condensation reaction with the aldehyde in the same manner as that for 2,5-xylenol, whereas those alkylphenols less reactive with the aldehyde, such as 2,4,6-trimethylphenol, cannot be removed by the method according to the present invention. Accordingly, when the starting xylenol mixture contains a substantial amount of alkyl phenols other than 2,3-, 2,4- and 2,5-xylenol, other separation methods, for example, distillation or recrystallization, are preferably used, e.g., more than about 1%, in combination with the method according to the present invention.

Any aldehyde which reacts with 2,5-xylenol to form a condensate can be used in the present invention including, for example, low molecular weight aliphatic aldehydes such as formaldehyde, acetaldehyde, propionaldehyde and butyraldehyde, as well as aromatic aldehydes such as benzaldehyde. Among these aldehydes, formaldehyde and acetaldehyde are preferred in view of their reactivity, selectivity, cost, yield and the utility of their condensates. The selected aldehyde can be used in any of its forms, such as an aqueous solution, alcohol solution trimer, polymer or acetal. when using the aldehyde in hydrous form such as an aqueous solution, the amount of water present in the reaction system can be controlled by the amount of water introduced by the aldehyde used into the reaction system. In any event, the amount of water in the condensation reaction system should be less than the saturation solubility based on the entire reaction mixture, so that a dual layer of crude 2,4-xylenol solution and water does not form in the reaction system.

The optimum amount of the aldehyde used depends more or less on the amount of 2,5-xylenol to be removed, the reaction conditions, etc., but it is desirable to select the reaction conditions such that 2,4-xylenol with high purity can be obtained by using the least amount of aldehyde as possible. Usually, the amount of aldehyde used is from 0.3 to 3 molar times (equivalents), preferably, from 0.3 to 2.0 molar times the amount of 2,5-xylenol contained in the starting mixture. The reaction is preferably continued until all of the aldehyde is consumed.

In the condensation reaction of the present invention, any aromatic sulfonic acid can be used as the catalyst, including, for example, benzene sulfonic acid, ortho-, metha- and para-toluene sulfonic acid and dibenzene sulfonic acid. Para-toluene sulfonic acid is the most preferred catalyst.

The amount of the catalyst used can vary widely but is usually within a range from 0.01 to 1 parts (0.01–1%) by weight, based on 100 parts by weight of the starting crude 2,4-xylenol. If the amount of the catalyst used is excessive, the purity of the 2,4-xylenol obtained may be lowered.

The reaction can be carried out over a wide temperature, e.g., from below room temperature to up to about 80 ° C. or higher, because the sulfonic acid is effective as a catalyst at low temperatures. Because the selectivity of the condensation reaction is higher at lower temperatures, the reaction is ordinarily not conducted at a temperature above 60 ° C. The optimum reaction temperature can be controlled by the presence of water. Thus, whereas the preferred temperature range is 20° to 40° C. in the absence of water, the preferred range is 20°–60° C. in the presence of water. Higher reaction temperatures are not preferred since 2,4-xylenol can react with the aldehyde with corresponding reduction in yield. Moreover, the purity of the recovered 2,4-xylenol may be lowered. Lower reaction temperatures are also not advantageous since the reaction rate is reduced, thereby requiring an extremely long reaction time.

When the condensation reaction according to the present invention is conducted in the presence of water, the amount of water added ordinarily should not exceed the saturation solubility of the xylenol isomer mixture at the reaction temperature. Preferably, from 2 to 20 parts by weight of water are present in the reaction system based on 100 parts by weight of the xylenol isomer mixture. Since it is usually desired to conduct the reaction at a temperature from 20° to 60° C., the solubility of the entire xylenol isomer mixture in water in this case is about from 5 to 20% and water is added in an amount preferably not exceeding this range. If an amount of water is added which exceeds its solubility, the reaction mixture separates into two layers and the reaction rate is extremely lowered, which is not advantageous.

The xylenol isomer mixture exhibits various solidification temperatures, depending on its composition. If the starting xylenol isomer mixture is solid at the temperature range selected for the condensation reaction, a solvent which does not adversely affect the reaction may be used. Suitable solvents include, for example, aromatic hydrocarbons such as benzene, toluene, xylene, cumene and mesitylene; alipatic hydrocarbons such as hexane, heptane and octane; halogenated hydrocarbons such as chlorobenzene, ortho-dichlorobenzene, chloroform, carbon tetrachloride and dichloroethane; etc.

Taking into consideration the purity and yield of purified 2,4-xylenol recovery rate, cost, performance of the solvent, etc., toluene is one of the most preferred solvents. When the starting xylenol isomer mixture is liquid at the selected reaction temperature, the reaction may also be carried out using a solvent as described above, if desired.

When using a solvent, the amount used is usually less than 500 parts by weight and, preferably, less than 200 parts by weight based on the 100 parts by weight of the crude 2,4-xylenol.

Since the dehydration-condensation reaction between xylenol and aldehyde is an equilibrium reaction, if the reaction product is directly subjected to distillation, 2,5-xylenol-aldehyde condensates formed in the reaction step undergo hydrolysis during distillation into 2,5-xylenol, which may intrude into the distillation solution, thereby reducing the purity of 2,4-xylenol. Accordingly, the acid used as the catalyst as described above has to be removed before distillation. Thus, the aromatic sulfonic acid is removed before distillation in the present invention, preferably by neutralization.

The aromatic sulfonic acid can be removed by water washing and liquid separation of the reaction mass after the end of the condensation reaction or by neutralization with a base. However, since acid removal by the neutralization has no substantial effect on the purity of the purification product in the present invention, the preferred method of isolating the purified 2,4-xylenol in accordance with the present invention is to neutralize the reaction product, e.g., with an excess amount of aqueous ammonia after the completion of the reaction followed by distillation. In the prior art purification method using hydrochloric acid as the catalyst described above, since the ammonium chloride formed upon neutralization with aqueous ammonia sublimates during distillation and intrudes into 2,4-xylenol, such a method cannot be used. The method according to the invention can be said extremely advantageous also from this point of view.

As has been described above, in the present invention, pure 2,4-xylenol can be obtained as a distillate by distillation, after neutralization of the reaction mixture with aqueous ammonia. After the neutralization and distillation, the xylenol-aldehyde condensates and the ammonium salt of aromatic sulfonic acid remain in the distillation pot. The condensates can be purified and recovered therefrom, if desired, in a conventional manner, such as water washing, recrystallization, etc., to separate the ammonium salt of aromatic sulfonic acid.

The present invention will be described more specifically referring to examples and comparative examples.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

To a 500 ml volume four-necked glass flask, 244.4 g of crude 2,4-xylenol of the composition shown in Table 1, 6.6 g of 90% para-formaldehyde and 0.2 g of p-toluene sulfonic acid were charged and reacted at a reaction temperature of 20° C. for 4 hours with stirring. Then, after neutralization by the addition of 0.1 ml of an aqueous 25% ammonia solution, distillation under a reduced pressure was conducted to obtain 196.1 g of a pure 2,4-xylenol fraction boiling at 104° C./21 mmHg, whose composition is shown in Table 1. The purity-converted recovery yield of 2,4-xylenol was 86.3%.

EXAMPLE 2

Follow the same procedure as in Example 1 except for changing the reaction temperature to 80° C. and the reaction time to one hour to obtain 195.0 g of purified 2,4-xylenol of the composition shown in Table 1.

EXAMPLE 3

Follow the same procedures as in Example 1 except for changing the reaction temperature to 0° C. and the reaction time to 20 hours to obtain 195.3 g of purified 2,4-xylenol of the composition shown in Table 1.

EXAMPLE 4

Follow the same procedures as in Example 1 except for changing 6.6 g of 90% p-formaldehyde to 17.2 g of an aqueous 35% formalin solution to obtain 193.6 g of purified 2,4-xylenol of the composition shown in Table 1.

EXAMPLE 5

Follow the same procedures as in Example 1 except for changing 6.6 g of 90% p-formaldehyde to 9.7 g of an aqueous 90% acetaldehyde solution to obtain 194.9 g of purified 2,4-xylenol of the composition shown in Table 1.

EXAMPLE 6

Follow the same procedures as in Example 1 except for changing 0.2 g of p-toluene sulfonic acid to 0.2 g of benzene sulfonic acid to obtain 195.7 g of purified 2,4-xylenol of the composition shown in Table 1.

EXAMPLE 7

To a 500 ml volume four-necked glass flask, 244.4 g of crude 2,4-xylenol of the composition shown in Table 1, 6.6 g of 90% para-formaldehyde, 0.2 g of p-toluene sulfonic acid and 200 ml of toluene were charged and reacted at a reaction temperature of 0° C. for 10 hours. After the reaction was over, 0.2 g of aqueous 25% ammonia and 50 ml of water were added with cooling. After stirring for one hour, the mixture was subjected to liquid separation. Then, after washing with 50 ml of water, toluene was removed by an evaporator. The residue was distilled under a reduced pressure to obtain 190.1 g of a purified 2,4-xylenol fraction being at 104° C./21 mmHg. The composition of the purified 2,4-xylenol, is shown in Table 1.

EXAMPLE 8

To a 500 ml volume four-necked glass flask, 244.4 g of crude 2,4-xylenol of the composition shown in Table 1; 17.2 g of 35% aqueous-formalin solution and 0.1 g of p-toluene sulfonic acid were charged and reacted at a reaction temperature of 20° C. for 4 hours while stirring. After the reaction was over, 200 ml of water was added and stirred sufficiently and then the resultant liquid was subject to separation. The oil layer was distilled under a reduced pressure to obtain 188.3 g of a purified 2,4-xylenol fraction boiling at 104° C./21 mmHg. The composition of the purified 2,4-xylenol was shown in Table 1.

TABLE I

| Crude 2,4-xylenol Example No. | Composition (%) | | | | | | | Purity-converted yield % |
|---|---|---|---|---|---|---|---|---|
| | 2,4- | 2,5- | 2,3- | 2,6- | p-[1] | TMP[2] | others | |
| | 91.8 | 6.9 | 0.7 | 0.3 | 0.1 | 0.1 | 0.1 | |
| 1 | 98.7 | 0.8 | 0.1 | t (3) | 0.1 | 0.1 | 0.2 | 86.3 |
| 2 | 97.5 | 1.9 | 0.1 | t | 0.1 | 0.2 | 0.2 | 84.7 |
| 3 | 99.5 | 0.2 | t | t | t | 0.1 | 0.2 | 86.6 |
| 4 | 98.8 | 0.7 | 0.1 | t | t | 0.2 | 0.2 | 85.2 |
| 5 | 99.0 | 0.7 | t | t | 0.1 | 0.1 | 0.1 | 86.0 |
| 6 | 98.8 | 0.8 | 0.1 | t | 0.1 | 0.1 | 0.1 | 86.2 |
| 7 | 99.5 | 0.2 | t | t | 0.1 | 0.1 | 0.1 | 84.3 |
| 8 | 98.6 | 0.9 | 0.1 | t | 0.1 | 0.1 | 0.2 | 82.7 |

[1] p- = p-cresol
[2] TMP = trimethylphenols
[3] t = trace amount

EXAMPLE 9

To a 500 ml volume four-necked glass flask, 244.4 g of crude 2,4-xylenol of the composition shown in Table 2, 19.3 g of 90% para-formaldehyde, 0.1 g of p-toluene sulfonic acid were charged and reacted at a reaction temperature of 20° C. for 5 hours. After the reaction was over, the reaction product was neutralized with an aqueous 25% ammonia and then distilled to obtain 175.6 g of purified 2,4-xylenol whose composition is shown in Table 2. The purity-converted recovery yield of 2,4-xylenol was 85%.

TABLE 2

| | 2,4- | 2,5- | 2,3- | 2,6- | p- | TMP | others |
|---|---|---|---|---|---|---|---|
| crude 2,4-xylenol | 82.5 | 15.2 | 1.0 | 1.0 | 0.1 | 0.1 | 0.1 |
| purified 2,4-xylenol | 97.5 | 2.2 | 0.1 | t | t | 0.1 | 0.1 |

COMPARATIVE EXAMPLE 1

The reaction was conducted according to U.S. Pat. No. 2,917,487. To a 500 ml volume four-necked flask made of glass, 244.4 g of crude 2,4-xylenol of the composition shown in Table 1 and 6.6 g of 90% paraformaldehyde were charged and kept at 100° C. Then, 40 ml of 36% hydrochloric acid was charged and the reaction was conducted at 100° C. for one hour. Then, after neutralization by the addition of 30 ml of aqueous 25% ammonia, the product was distilled to obtain 194.8 g of fractions boiling at 104° C./21 mmHg. The fractions containing 400 ppm of ammonium chloride were opaque and the 2,4-xylenol purity was 94.9%. Main impurity was 2,5-xylenol.

EXAMPLE 10

To a 500 ml volume four-necked glass flask, 244.4 g of crude 2,4-xylenol of the composition shown in Table 1, 6.6 g of 90% para-formaldehyde, 0.2 g of p-toluene sulfonic acid, 200 ml of toluene and 200 g of water were charged and reacted at a reaction temperature of 40° C. for 10 hours. After the reaction was over, the reaction product was neutralized with 1 ml of aqueous 25% ammonia and then distilled to obtain 194.5 g of pure 2,4-xylenol fractions boiling at 104° C./21 mmHg (purified 2,4-xylenol) whose composition is shown in Table 3. The purity-converted recovery yield of 2,4-xylenol was 85.9%.

TABLE 3

| | crude 2,4-xylenol | purified 2,4-xylenol |
|---|---|---|
| 2,4-xylenol | 91.8% | 99.1% |
| 2,5- | 6.9 | 0.6 |
| 2,3 | 0.7 | t (3) |
| 2,6- | 0.3 | t |
| p- (1) | 0.1 | 0.1 |
| TMP (2) | 0.1 | 0.1 |
| other | 0.1 | 0.1 |

(1) p- = p-cresol
(2) TMP = trimethylphenols
(3) t = trace amounts

COMPARATIVE EXAMPLE 2

The reaction was conducted according to U.S. Pat. No. 2,917,487. Into a 500 ml volume four-necked glass flask, 244.4 g of crude 2,4-xylenol of the composition shown in Table 1 and 6.6 g of 90% para-formaldehyde were charged and kept at 100° C. Then, 400 ml of 36% hydrogen chloride were charged and the reaction was conducted at 100° C. for one hour. Then, after neutralization with 30 ml of aqueous 25% ammonia, the product was distilled to obtain 194.8 g of a fraction boiling at 104° C./21 mmHg. The fractions containing 400 ppm of ammonium chloride were opaque and the 2,4-xylenol purity was 94.9%. Main impurity was 2,5-xylenol. The purity-converted recovery yield was 82.4%.

EXAMPLE 11

To a 500 ml volume four-necked glass flask, 244.4 g of crude 2,4-xylenol of the composition shown in Table 2, 19.3 g of 90% para -formaldehyde, 0.2 g of p-toluene sulfonic acid, 200 ml of toluene and 20 g of water were charged and reacted and processed following the same procedures as in Example 10 to obtain 173.3 g of pure 2,4-xylenol of the composition shown in table 4. The purity-converted recovery yield of 2,4-xylenol was 85%.

TABLE 4

| | 2,4- | 2,5- | 2,3- | 2,6- | p- | TMP | others |
|---|---|---|---|---|---|---|---|
| crude 2,4-xylenol | 82.5 | 15.2 | 1.0 | 1.0 | 0.1 | 0.1 | 0.1 |
| purified 2,4-xylenol | 98.9 | 0.8 | 0.1 | t | t | 0.1 | 0.1 |

EXAMPLE 12

Reaction and processing were conducted in the same manner as in Example 10, except for replacing 6.6 g of 90% p-formaldehyde with 17.0 g of 35% formalin and changing the amount of water added from 20 to 10 g to obtain 194.4 g of pure 2,4-xylenol whose composition was 99.2 % of 2,4-xylenol and 0.6% of 2,5-isomer. The purity-converted yield was 85.9%.

EXAMPLE 13

To a 500 ml volume four-necked glass flask, 244.4 g of crude 2,4-xylenol of the composition shown in Table 1, 6.6 g of 90% para-formaldehyde, 0.2 g of p-toluene sulfonic acid and 30 g of water were charged and reacted at a reaction temperature of 60° C. for 10 hours. After the reaction was over, they were processed in the same manner as in Example 10 to obtain 194.0 g of purified 2,4-xylenol whose composition was 98.8% of 2,4-xylenol and 0.8% of 2,5-isomer. The purity-converted yield was 85.4%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of purifying 2,4-xylenol consisting essentially of a mixture of 2,4-xylenol and 2,5-xylenol which comprises the steps of reacting, in the presence of an acidic catalyst, the mixture with a low molecular weight monofunctional aldehyde which reacts with 2,5-xylenol to form a condensate, in an amount effective to react with substantially all of the 2,5-xylenol, and thereafter in the absence of the acidic catalyst, separating the 2,4-xylenol from the thus-produced 2,5-xylenol-aldehyde condensate, the improvement wherein the acidic catalyst is an aromatic sulfonic acid.

2. A method according to claim 1, wherein the reaction mixture is conducted in the presence of an amount of water less than that which effects separation of the reaction mixture into an aqueous layer and a crude 2,4-xylenol layer.

3. A method according to claim 1, wherein the reaction is conducted in the absence of water.

4. A method according to claim 1, wherein the starting mixture contains from 80 to 95% by weight of 2,4-xylenol and the thus-purified 2,4-xylenol has a purity higher than 95% by weight.

5. A method according to claim 1, wherein the reaction is conducted at a temperature of up to 60° C.

6. A method according to claim 1, wherein the reaction is conducted in the presence of water and at a temperature of from 20° to 60 ° C.

7. A method according to claim 1, wherein the reaction is conducted in the absence of water and at a temperature of from 20° to 50 ° C.

8. A method according to claim 1, wherein the amount of the aromatic sulfonic acid employed is from 0.01 to 1.0 parts by weight based on 100 parts by weight of the crude 2,4-xylenol.

9. A method according to claim 2, wherein the amount of water present in the reaction mixture is from 2 to 20 parts by weight based on 100 parts by weight of the starting mixture.

10. A method according to claim 1, wherein the aromatic sulfonic acid is p-toluene sulfonic acid.

11. A method according to claim 1, wherein the aldehyde is para-formaldehyde.

12. A method according to claim 1, wherein the 2,4-xylenol is separated by distillation.

13. A method according to claim 1, wherein the acidic catalyst is neutralized with ammonia prior to separation of the 2,4-xylenol.

14. A method according to claim 1, wherein the starting mixture consists essentially of 80–95% by weight of 2,4-xylenol and the remainder 2,5-xylenol, the reaction mixture is aqueous, the reaction is conducted at 20° to 60° C., the amount of aromatic sulfonic acid employed is from 0.01 to 1% by weight, based on the starting crude 2,4-xylenol, the amount of aldehyde employed is from 0.3 to 2.0 molar equivalents of the 2,5-xylenol present in the starting mixture, the purified 2,4-xylenol is removed by distillation, the aromatic sulfonic acid is neutralized with ammonia prior to distillation.

15. A method according to claim 14, wherein the aromatic sulfonic acid is p-toluene sulfonic acid.

16. A method according to claim 14, wherein the aldehyde is para-formaldehyde.

17. A method according to claim 1, wherein the aldehyde is formaldehyde, acetaldehyde, propionaldehyde, butyraldehyde or benzaldehyde.

18. A method according to claim 17, wherein the acidic catalyst is neutralized with ammonia prior to separation of the 2,4-xylenol and wherein the 2,4-xylenol is separated by distillation.

19. A method according to claim 14, wherein the aldehyde is formaldehyde, acetaldehyde, propionaldehyde, butyraldehyde or benzaldehyde.

* * * * *